(12) United States Patent
Chang et al.

(10) Patent No.: US 12,169,662 B2
(45) Date of Patent: Dec. 17, 2024

(54) VEHICLE AND CONTROL METHOD THEREOF

(71) Applicants: Hyundai Motor Company, Seoul (KR); Kia Corporation, Seoul (KR)

(72) Inventors: Kyoung-Jin Chang, Gyeonggi-do (KR); Dong Chul Park, Gyeonggi-do (KR); Jinsung Lee, Gyeonggi-do (KR); Sangjin Hong, Gyeonggi-do (KR)

(73) Assignees: Hyundai Motor Company, Seoul (KR); Kia Corporation, Seoul (KR)

(*) Notice: Subject to any disclaimer, the term of this patent is extended or adjusted under 35 U.S.C. 154(b) by 240 days.

(21) Appl. No.: 17/519,802

(22) Filed: Nov. 5, 2021

(65) Prior Publication Data

US 2022/0269474 A1 Aug. 25, 2022

(30) Foreign Application Priority Data

Feb. 22, 2021 (KR) .................. 10-2021-0023239

(51) Int. Cl.
*G06F 3/16* (2006.01)
*A61M 21/00* (2006.01)
*G06V 20/59* (2022.01)
*G06V 40/16* (2022.01)
*H04R 3/00* (2006.01)

(52) U.S. Cl.
CPC ............. *G06F 3/165* (2013.01); *A61M 21/00* (2013.01); *G06V 20/597* (2022.01); *G06V 40/166* (2022.01); *H04R 3/00* (2013.01); *A61M 2021/0027* (2013.01); *A61M 2205/3306* (2013.01); *A61M 2230/06* (2013.01); *A61M 2230/65* (2013.01); *H04R 2499/13* (2013.01)

(58) Field of Classification Search
CPC ....... H04R 3/00; H04R 2499/13; G06F 3/165; G06V 20/597; G06V 40/166; A61M 21/00; A61M 2021/0027; A61M 2205/3306; A61M 2230/06; A61M 2230/04; A61M 2230/65; G10K 15/02
See application file for complete search history.

(56) References Cited

U.S. PATENT DOCUMENTS

| | | | |
|---|---|---|---|
| 2015/0199955 A1 | 7/2015 | Draganic | |
| 2018/0090125 A1 | 3/2018 | Yeung | |
| 2018/0279881 A1* | 10/2018 | McCalmont | ....... A61B 5/14532 |
| 2020/0175719 A1* | 6/2020 | Wright | ..................... G06T 5/20 |

(Continued)

FOREIGN PATENT DOCUMENTS

| | | |
|---|---|---|
| JP | 2020-163936 A | 10/2020 |
| KR | 101535013 B1 | 7/2015 |

(Continued)

*Primary Examiner* — Jason R Kurr
(74) *Attorney, Agent, or Firm* — Fox Rothschild LLP

(57) ABSTRACT

A vehicle is provided and includes a camera that photographs a face of a driver, a sensor that obtains skin information of the driver, a speaker, and a controller. The controller determines a physical condition of the driver based on at least one of a face image of the driver and the skin information of the driver, determines a sound source and a parameter based on the physical condition of the driver, generates a driving sound by reflecting driving information of the vehicle in the sound source and the parameter, and operates the speaker to output the driving sound.

19 Claims, 9 Drawing Sheets

(56) References Cited

U.S. PATENT DOCUMENTS

| | | | | |
|---|---|---|---|---|
| 2020/0334479 A1* | 10/2020 | Szczerba | ................ | G06F 3/013 |
| 2021/0097408 A1* | 4/2021 | Sicconi | ................ | G06N 20/00 |
| 2021/0114603 A1* | 4/2021 | Dadam | ................ | B60W 10/30 |
| 2021/0269046 A1* | 9/2021 | Hashimoto | ............ | G06V 40/70 |

FOREIGN PATENT DOCUMENTS

| | | |
|---|---|---|
| KR | 101547938 B1 | 8/2015 |
| KR | 101744742 B1 | 6/2017 |
| KR | 2018-0020399 A | 2/2018 |
| KR | 101848779 B1 | 4/2018 |
| KR | 102006851 B1 | 8/2019 |
| KR | 102051542 B1 | 1/2020 |
| KR | 2020-0075144 A | 6/2020 |

\* cited by examiner

VEHICLE AND CONTROL METHOD THEREOF

CROSS-REFERENCE TO RELATED APPLICATION(S)

This application is based on and claims priority under 35 U.S.C. § 119 to Korean Patent Application No. 10-2021-0023239, filed on Feb. 22, 2021, in the Korean Intellectual Property Office, the disclosure of which is incorporated by reference herein in its entirety.

BACKGROUND

1. Field of the Disclosure

The disclosure relates to a vehicle and a control method thereof.

2. Description of the Related Art

In modern society, vehicles are the most used means of transportation, and the number of vehicles is increasing. Although in the past, the vehicle did not have a meaning beyond a means of transportation, in modern society, the vehicle is more used as a means of expressing oneself or enjoying a drive beyond a means of transportation. Accordingly, more people enjoy speed like motorbikes and racing vehicles, and people who enjoy such speed feel a lot of excitement not only from the sense of speed that comes from the speed of a vehicle, but also from the operation sound and vibration sound generated from an engine of the vehicle. Therefore, some drivers may modify the engine to obtain the driving sound desired by the driver.

In particular, in the case of an electric vehicle, since the operation sound and vibration sound are not generated by the engine of the vehicle, the driving sound artificially generated through a speaker may be output. However, since the driving sound provided to a vehicle is a driving sound designed in advance by a manufacturer, it is difficult to satisfy the demand of a driver.

SUMMARY

It is an aspect of the disclosure to provide a vehicle capable of determining a physical condition of a driver and generating a driving sound based on the physical condition of the driver and driving information of the vehicle, and a control method thereof.

Additional aspects of the disclosure will be set forth in part in the description which follows and, in part, will be obvious from the description, or may be learned by practice of the disclosure.

In accordance with an aspect of the disclosure, a vehicle may include a camera configured to photograph a face of a driver, a sensor configured to obtain skin information of the driver, a speaker, and a controller configured to determine a physical condition of the driver based on at least one of a face image of the driver and the skin information of the driver, determine a sound source and a parameter based on the physical condition of the driver, generate a driving sound by reflecting driving information of the vehicle in the sound source and the parameter, and operate the speaker to output the driving sound.

The vehicle may further include a memory provided to store the sound source for each of the physical conditions and matching data of the parameter for each of the physical conditions. The controller may be configured to receive the sound source and the parameter from the memory in real time based on the physical condition. The controller may be configured to apply an Eulerian video magnification framework to the face image, extract a blood flow image from the face image, and estimate a pulse rate of the driver based on the blood flow image.

The controller may be configured to derive a spatiotemporal slice of a blood flow based on the face image. The skin information may include a galvanic skin response (GSR). The controller may be configured to perform at least one of noise cancellation in data for the galvanic skin response, normalization, and selection of data satisfying a predetermined criterion. The controller may be configured to determine at least one of a tension state of the driver, a dehydration state of the driver, and a fatigue state of the driver. The controller may determine the physical condition using a support vector machine (SVM), which is an artificial intelligence algorithm. The driving information may include at least one of a rotation per minute (RPM) of a motor of the vehicle, a speed of the vehicle, an acceleration of the vehicle, and a pedal effort of the vehicle.

In accordance with another aspect of the disclosure, a control method of a vehicle may include determining a physical condition of a driver based on at least one of a face image of the driver and skin information of the driver, determining a sound source and a parameter based on the physical condition, generating a driving sound by reflecting driving information of the vehicle in the sound source and the parameter, and outputting the driving sound.

The control method may further include storing the sound source for each of the physical conditions and matching data of the parameter for each of the physical conditions, in a memory. The control method may further include receiving the sound source and the parameter from a memory in real time based on the physical condition. The control method may further include applying an Eulerian video magnification framework to the face image, extracting a blood flow image from the face image, and estimating a pulse rate of the driver based on the blood flow image.

The control method may further include deriving a spatiotemporal slice of a blood flow based on the face image. The skin information may include a galvanic skin response (GSR). The control method may further include performing at least one of noise cancellation in data for the galvanic skin response, normalization, and selection of data satisfying a predetermined criterion. The control method may further include determining at least one of a tension state of the driver, a dehydration state of the driver, and a fatigue state of the driver. The control method may further include determining the physical condition using a support vector machine (SVM), which is an artificial intelligence algorithm. The driving information may include at least one of a rotation per minute (RPM) of a motor of the vehicle, a speed of the vehicle, an acceleration of the vehicle, and a pedal effort of the vehicle.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
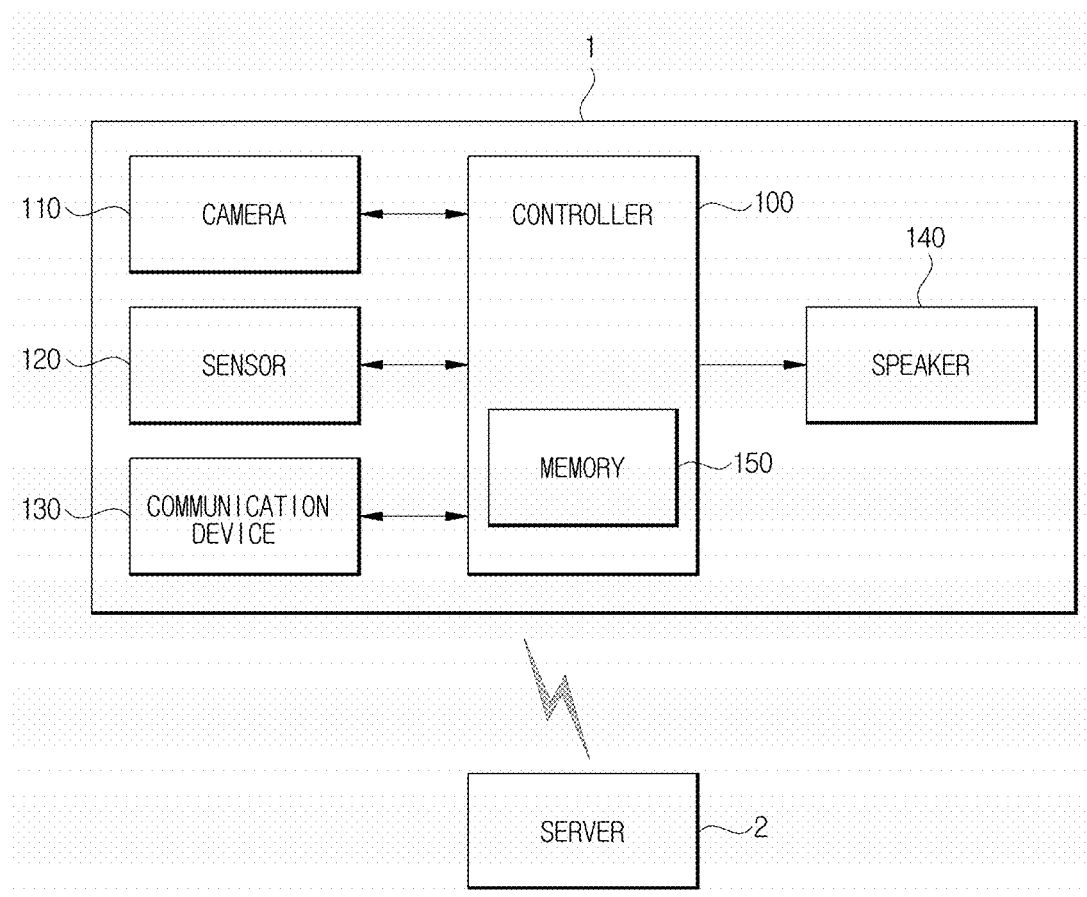
FIG. 1 is a control block diagram of a vehicle according to an embodiment of the disclosure.

Throughout the specification, like reference numerals refer to like elements. This specification does not describe all the elements of the embodiments, and duplicative contents between general contents or embodiments in the technical field of the disclosure will be omitted. The terms 'part,' 'module,' 'member,' and 'block' used in this specification may be embodied as software or hardware, and it is also possible for a plurality of 'parts,' 'modules,' 'members,' and 'blocks' to be embodied as one component, or one 'part,' 'module,' 'member,' and 'block' to include a plurality of components according to embodiments.

Throughout the specification, when a part is referred to as being "connected" to another part, it includes not only a direct connection but also an indirect connection, and the indirect connection includes connecting through a wireless network. Also, when it is described that a part "includes" an element, it means that the element may further include other elements, not excluding the other elements unless specifically stated otherwise.

In the present specification, it will also be understood that when an element is referred to as being "on" or "over" another element, it may be directly on the other element or intervening elements may also be present. The terms 'first,' 'second,' etc. are used to distinguish one element from another element, and the elements are not limited by the above-mentioned terms. The singular forms "a," "an," and "the" include plural referents unless the context clearly dictates otherwise. In each step, an identification numeral is used for convenience of explanation, the identification numeral does not describe the order of the steps, and each step may be performed differently from the order specified unless the context clearly states a particular order.

Hereinafter, the disclosure will be described in detail with reference to the accompanying drawings. FIG. 1 is a control block diagram of a vehicle according to an embodiment of the disclosure.

Referring to FIG. 1, a vehicle 1 may include a camera 110 configured to photograph a face of a driver, a sensor 120 configured to obtain skin information of the driver, a communication device (CAN: Controller Area Network) 130, a speaker 140, and a controller 100 configured to determine a physical condition of the driver based on at least one of a face image of the driver and the skin information of the driver, determine a sound source and a parameter based on the physical condition of the driver, generate a driving sound by reflecting driving information of the vehicle in the sound source and the parameter, and control the speaker 140 to output the driving sound.

The camera 110 may be disposed above a driver seat, but is not limited thereto as long as the camera 110 is in a position to obtain the face image of the driver. The camera 110 may be configured to obtain a face image by photographing the face of the driver and may transmit the obtained face image to the controller 100. The sensor 120 may include a sensor mounted on a body of the driver, such as a finger of the driver, which may be easily attached and detached, to measure a galvanic skin response (GSR). More specifically, by the measurement of the galvanic skin response, which measures an electrical conductivity of a skin, it may be easier to determine psychological and physical arousal state of the driver associated with a sympathetic nervous system of the driver.

The sensor 120 may be configured to measure the galvanic skin response of the driver and transmit the measurement result to the controller 100. Additionally, the sensor 120 may be a body temperature sensor installed on the driver seat of the vehicle to detect a body temperature of the driver, may be an electrocardiogram sensor provided on a steering wheel to detect an electrocardiogram signal from a hand of the driver, and may include a receiving device that obtains a bio-signal from a wearable device of the driver. For example, the bio-signal may include an EMG signal, an electrocardiogram signal, an electroencephalogram signal, a safety level signal, and the like.

The sensor 120 may be disposed at various locations within the vehicle. For example, the sensor 120 may be provided in a seat, a seat belt, the steering wheel, a handle provided on a door, and the like, but is not limited thereto. The communication device 130 may be configured to receive information such as a motor RPM (rotate per minute) of an electric vehicle, a speed of the vehicle 1, an acceleration of the vehicle 1, and an opening degree of an accelerator pedal of the vehicle 1 and transmit the information to the controller 100.

The communication device 130 may include one or more components that enable communication with an external device, and may include, for example, at least one of a short-range communication module, a wired communication module, and a wireless communication module. Additionally, the communication device 130 may include one or more components that enable communication with the inside of the vehicle, and may include, for example, at least one of a short-range communication module, a wired communication module, and a wireless communication module. For example, the short-range communication module may include various short-range communication modules that transmit and receive signals using a wireless communication network in a short distance such as a Bluetooth module, an infrared communication module, an RFID (Radio Frequency Identification) communication module, a WLAN (Wireless Local Access Network) communication module, an NFC communication module, and a Zigbee communication module.

For example, the wired communication module may include various wired communication modules such as a CAN (Controller Area Network) communication module, a LAN (Local Area Network) module, a WAN (Wide Area Network) module, or a VAN (Value Added Network) module, as well as various cable communication modules such as a USB (Universal Serial Bus), an HDMI (High Definition Multimedia Interface), a DVI (Digital Visual Interface), an RS-232 (recommended standard 232), power line communication, and a POTS (plain old telephone service). The wireless communication module, in addition to the Wi-Fi module and the wireless broadband module, may include wireless communication modules supporting various wireless communication methods such as a GSM (Global System for Mobile Communication), a CDMA (Code Division Multiple Access), a WCDMA (Wideband Code Division Multiple Access), a UMTS (Universal Mobile Telecommunications System), a TDMA (Time Division Multiple Access), and LTE (Long Term Evolution). The wireless communication module may include a wireless communication interface including an antenna and a transmitter for transmitting a signal. The wireless communication module may further include a signal conversion module that modulates a digital control signal output from the controller 200 through the wireless communication interface into an analog wireless signal according to the control of the controller 200.

The speaker 140 may be disposed on both doors of the vehicle, but is not limited thereto as long as the driver may hear a sound output from the inside of the vehicle. For example, the speaker 140 may be configured to output a control signal (electrical signal) received from the controller 110 as a driving sound. The speaker 140 may include components such as a voice coil and an amplifier that adjusts a volume of an output sound by adjusting a magnitude of a current supplied to the voice coil.

A memory 150 may be configured to store a plurality of sound sources classified depending on physical conditions of the driver, such as a sound source for each physical condition of the driver and a parameter for each physical condition of the driver. For example, the memory 150 may be configured to store a sound source corresponding to a case in which the physical condition of the driver is in a temporary tense state, and may store a sound source corresponding to a case in which the physical condition of the driver is in a dehydration state. In addition, the memory 150 may be configured to store a sound source corresponding to a case in which the physical condition of the driver is in a state of accumulated fatigue, and in this case, determine a fatigue level of the driver again and store sound sources corresponding to fatigue levels of the driver, respectively. The memory 150 may be implemented as a separate chip, or may be implemented as a single chip together with a processor corresponding to the controller 100.

A program for determining an emotional state, gender and age of the driver stored in the memory 150 may include an artificial intelligence algorithm (artificial neural network model) such as a convolutional neural networks (CNN) algorithm, a generative adversarial networks (GAN) algorithm, a recurrent neural networks (RNN) algorithm, a long short-term memory (LSTM) algorithm, which is a type of the RNN algorithm, and a region-based convolutional neural networks (R-CNN) algorithm.

In order to store various information, the memory 150 may be implemented as at least one of a non-volatile memory device such as a cache, a ROM (Read Only Memory), a PROM (Programmable ROM), an EPROM (Erasable Programmable ROM), an EEPROM (Electrically Erasable Programmable ROM), and a flash memory, a volatile memory device such as a RAM (Random Access Memory), and a storage medium such as a HDD (hard disk drive) and a CD-ROM, but is not limited thereto.

The controller 100 may include the at least one memory 150 for storing various programs such as a program for generating a driving sound and a program for controlling the speaker 140. Additionally, the controller 100 may include at least one processor (not shown) capable of executing the programs stored in the memory 150. The controller 100 may be configured to receive the face image of the driver photographed from the camera 110. The controller 100 may be configured to extract a blood flow image by applying an Eulerian video magnification framework to the face image of the driver.

The controller 100 may be configured to enlarge the extracted blood flow image and derive a spatiotemporal slice of the blood flow based on the enlarged blood flow image. The controller 100 may be configured to estimate a pulse rate of the driver using the blood flow image and the spatiotemporal decomposition image of the blood flow. The controller 100 may be configured to receive the skin information of the driver including the galvanic skin response from the sensor 120. The sensor 120 for measuring the galvanic skin response may be a galvanic skin response (GSR) recognition sensor. The controller 100 may be configured to analyze the skin information of the driver received from the sensor 120. For example, the controller 100 may be configured to cancel a noise from the skin information, may perform normalization of the skin information, and analyze the skin information by selecting meaningful data from the skin information.

The controller 100 may be configured to determine bio-signal characteristics related to the physical condition of the driver through a current waveform analysis of the galvanic skin response of the driver received from the sensor 120, and determine bio-signal characteristics of the driver based on the pulse rate of the driver estimated from the face image of the driver and the galvanic skin response of the driver. For example, the controller 100 may be configured to determine whether the driver is temporarily nervous, whether the driver is dehydrated, how much fatigue the driver has accumulated, or the like based on the bio-signal characteristics. The controller 100 may be configured to comprehensively determine a physical condition of the driver using a support vector machine (SVM), which is an artificial intelligence algorithm, based on the bio-signal characteristics of the driver.

In particular, the controller 100 may be configured to comprehensively determine a physical condition of the driver based on comprehensive analysis data for the physical condition of the driver based on the artificial intelligence algorithm and various learning models. The comprehensive analysis data for the physical condition of the driver based on the artificial intelligence algorithm and the various learning models may be received from an external server 2. In particular, the external server 2 may be a cloud server, but is not limited thereto. For example, the controller 100 may be configured to determine that the physical condition of the driver is in a state in which the driver is very excited and somewhat tired, and may receive a sound source and a parameter suitable for this state of the driver from the memory 150.

The controller 100 may be configured to receive a sound source and a parameter corresponding to the physical condition of the driver from the memory 150 based on the physical condition of the driver. Particularly, the controller 100 may be configured to receive a sound source and a parameter corresponding to the physical condition of the driver in real time based on the physical condition of the driver that changes in real time. Additionally, the controller 100 may be configured to receive a sound source and a parameter corresponding the physical condition of the driver every predetermined period based on the physical condition of the driver that changes every predetermined period.

For example, the controller 100 may be configured to determine a physical condition of the driver every two minutes, receive a sound source and a parameter corresponding thereto, and generate a driving sound by synthesizing a sound source and a parameter signal, thereby outputting a newly generated driving sound every two minutes. The controller 100 may be configured to generate a driving sound by reflecting the driving information of the vehicle 1 in the sound source and the parameter.

More specifically, the controller 100 may be configured to generate a driving sound by reflecting at least one of a motor RPM, torque, accelerator pedal sensor (APS), speed, acceleration, and pedal effort, which are the driving information of the vehicle 1. For example, the controller 100 may be configured to generate a driving sound by synthesizing a signal corresponding to the pedal effort with the sound source. Additionally, the controller 100 may be configured to generate a driving sound by reflecting a tuning variable of the sound source. More specifically, the controller 100 may generate a driving sound by reflecting at least one of a pitch increase rate, pitch random variation, grain size, grain location, filter type, filter frequency, and shepard tone level, which are the tuning variables of the sound source.

The controller 100 may be configured to adjust the driving sound to be output from the speaker 140. The controller 100 may be implemented as a memory for storing an algorithm for controlling the operations of components inside the vehicle 1 or data for a program reproducing the algorithm and a processor (not shown) for performing the above-described operations using data stored in the memory. In particular, the memory may be implemented as a separate chip from the processor or may be implemented as a single chip with the processor.

The vehicle 1 according to an embodiment as described above does not always provide the same driving sound in the vehicle 1, but may provide various driving sounds automatically reflecting the physical condition of the driver. Accordingly, a driving pleasure may be provided to the driver, thereby improving the marketability of the vehicle, and in particular, in the field of a future mobility such as a shared vehicle, various driving sounds may be provided to suit various drivers.

Additionally, as the vehicle 1 provides a driving sound suitable for a physical condition of the driver after recognizing the physical condition of the driver during driving, the driver may drive while listening to a driving sound having a calm and bright feeling when tired, may drive while listening to a driving sound having a cheerful and sporty feeling when excited, and may drive while listening to a driving sound having a soft and emotional feeling when depressed, so that a feeling of fatigue of the driver may be alleviated, and a feeling of pleasure of the driver may be doubled.

Figure 2A:
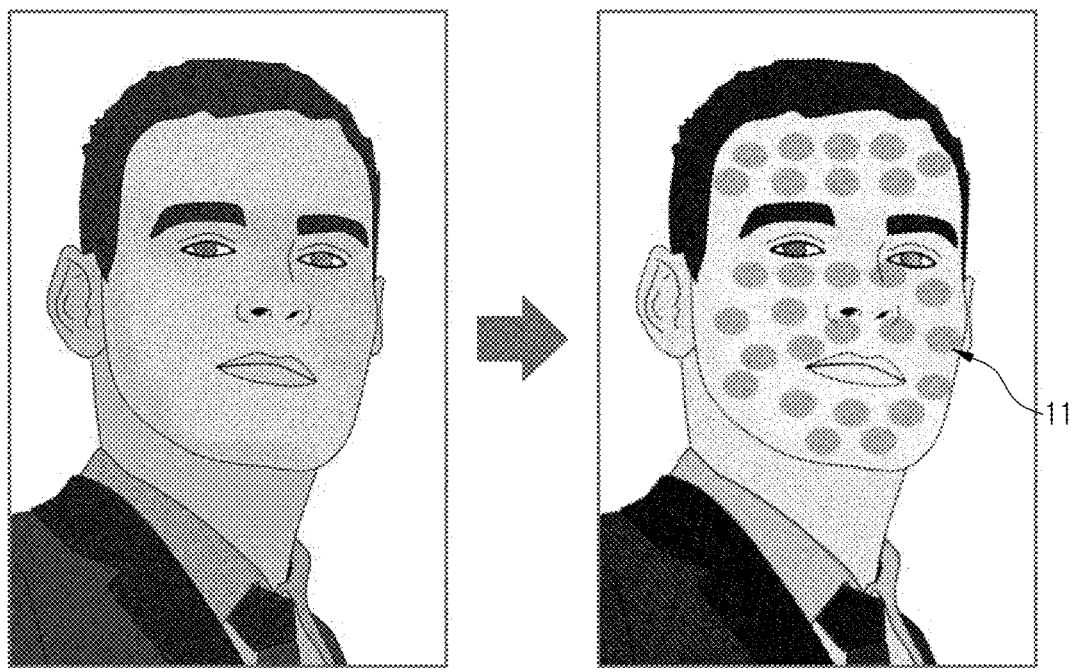
FIGS. 2A-2B illustrate a face image of a driver according to an embodiment of the disclosure.
Figure 2B:
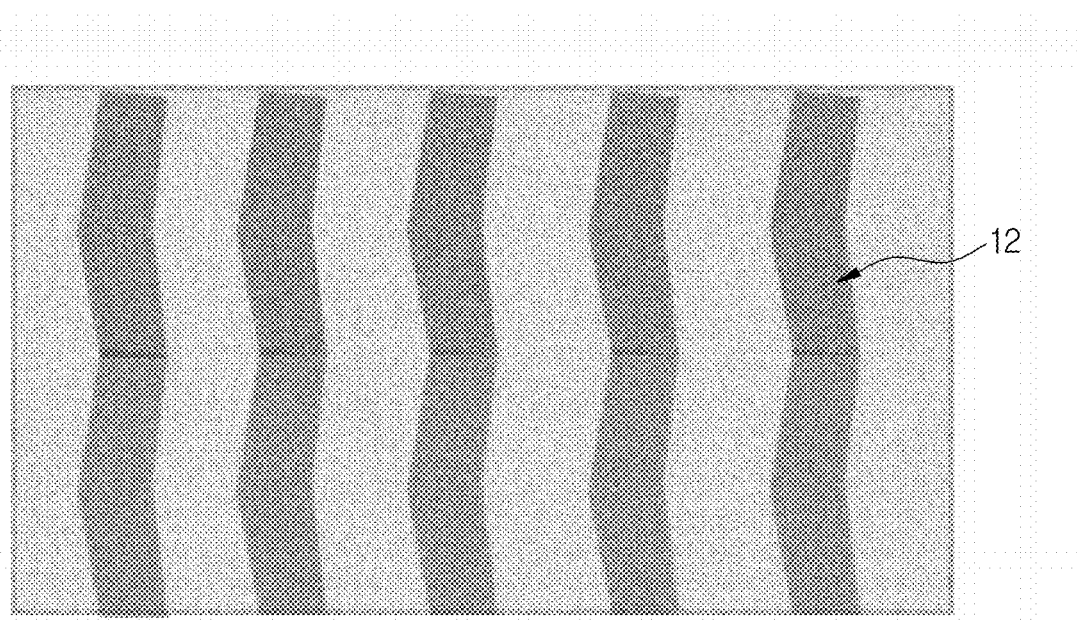

FIGS. 2A-2B illustrate a face image of a driver according to an embodiment of the disclosure. Referring to FIG. 2A, the vehicle 1 may be configured to capture a face image of the driver through the camera 110. The vehicle 1 may be configured to check a blood flow 11 by applying the Eulerian video magnification framework to the photographed face image of the driver, and extract a blood flow image. Referring to FIG. 2B, the vehicle 1 may be configured to enlarge an extracted blood flow image 12. The vehicle 1 may be configured to derive a spatiotemporal slice of the blood flow 11 based on the enlarged blood flow image 12.

Figure 3A:
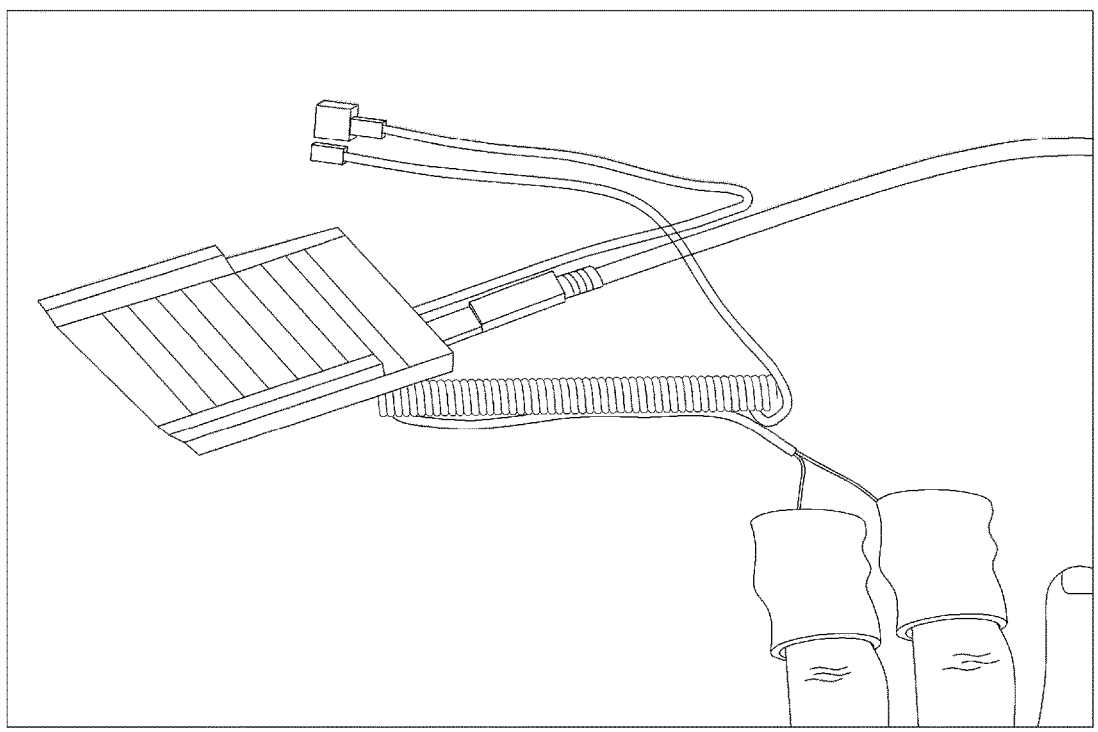
FIGS. 3A-3B illustrate an apparatus for measuring a skin state and a result graph according to an embodiment of the disclosure.
Figure 3B:
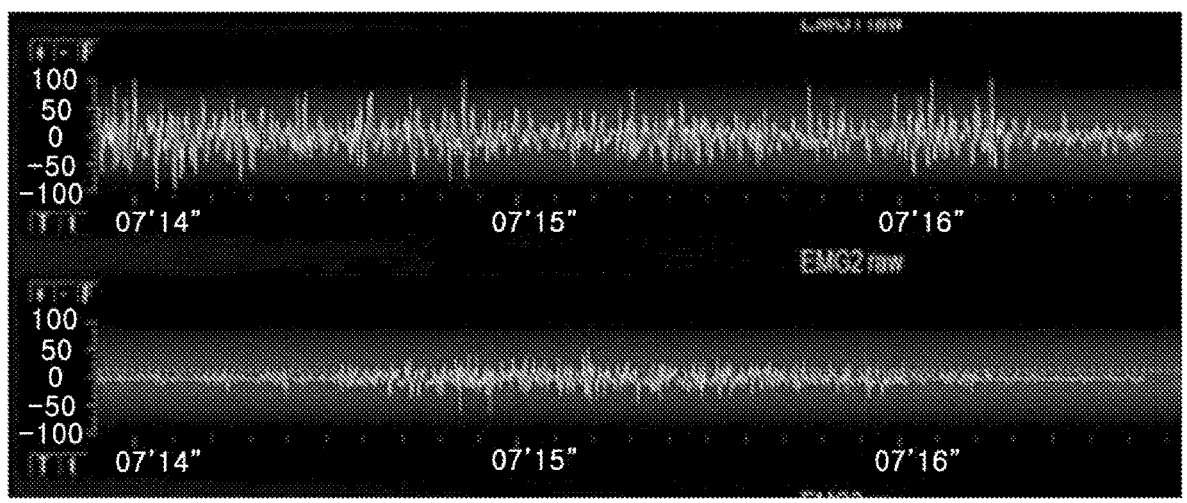

FIGS. 3A-3B illustrate an apparatus for measuring a skin state and a result graph according to an embodiment of the disclosure. Referring to FIG. 3A, the vehicle 1 may include the sensor 120 mounted on a body of the driver, such as a finger of the driver, which may be more easily attached and detached, to measure the galvanic skin response (GSR) of the driver.

More specifically, referring to FIG. 3B, the vehicle 1 may be configured to analyze a current waveform for the galvanic skin response of the driver measured from the sensor 120. For example, for the vehicle 1 to cancel a noise and utilize a meaningful bio-signal, the bio-signal may be filtered by a first bandpass filter passing signals in a first frequency band and a second bandpass filter passing signals in a second frequency band. In particular, the first frequency band may be a low frequency region, and the second frequency band may be a high frequency region.

Figure 4:
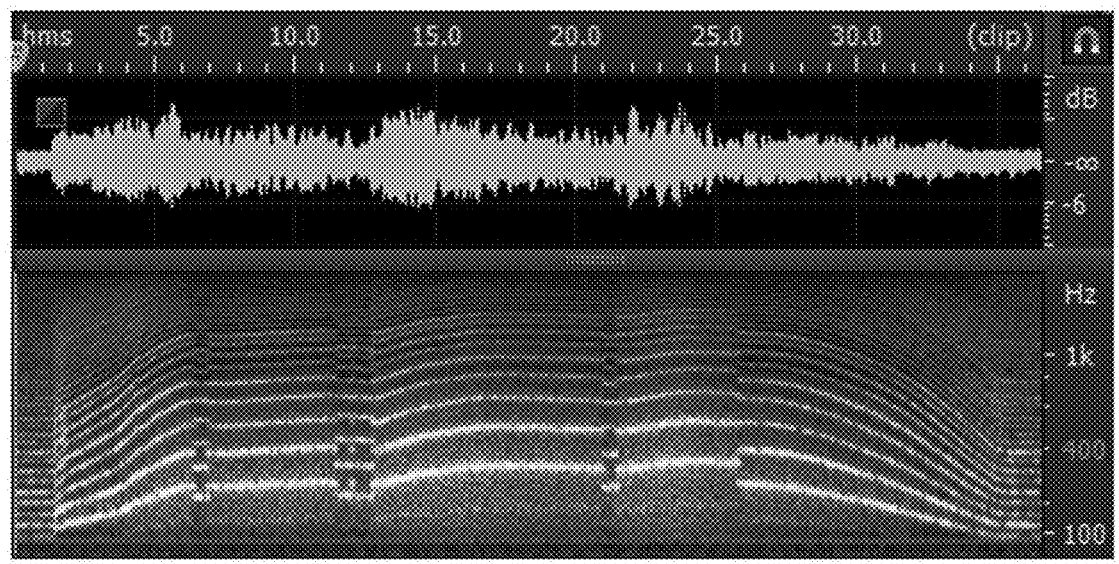
FIG. 4 is a graph illustrating a process of synthesizing driving sounds according to an embodiment of the disclosure.

FIG. 4 is a graph illustrating a process of synthesizing driving sounds according to an embodiment of the disclosure. Referring to FIG. 4, the vehicle 1 may be configured to generate a driving sound by reflecting the driving information of the vehicle 1 in the sound source and the parameter received from the memory 150, and accordingly, the vehicle 1 may be configured to receive at least one information of the motor RPM, torque, accelerator pedal sensor (APS), speed, acceleration, and pedal effort, which are the driving information of the vehicle 1, through the communication device 130.

Additionally, the vehicle 1 may be configured to generate a driving sound by reflecting the tuning variable of the sound source received from the memory 150 together. The tuning variable of the sound source may include at least one of the pitch increase rate, pitch random variation, grain size, grain location, filter type, filter frequency, and shepard tone level. For example, the vehicle 1 may be configured to generate a driving sound by synthesizing a signal corresponding to any one of the driving information of the vehicle 1 with a sound source. In particular, the vehicle 1 may be configured to generate a driving sound that is changed in real time by reflecting the driving information of the vehicle 1 that is changed in real time and synthesizing a signal corresponding to the changed driving information with a sound source. Additionally, the vehicle 1 may be configured to generate a driving sound by reflecting any one of the tuning variables of the sound source to the driving sound synthesized with a signal corresponding to the driving information of the vehicle 1 and synthesizing the reflected tuning variable together.

Figure 5:
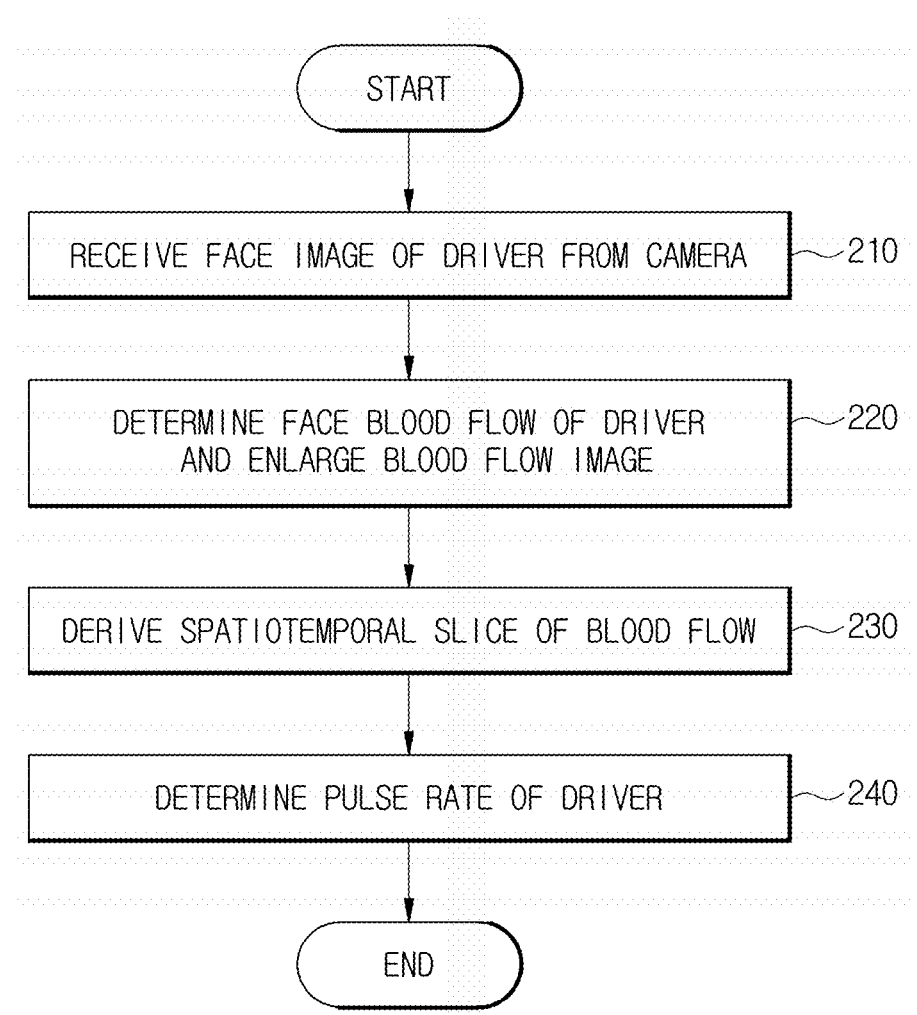
FIG. 5 illustrates a pulse rate analysis method based on the face image of the driver according to an embodiment of the disclosure.

FIG. 5 illustrates a pulse rate analysis method based on the face image of the driver according to an embodiment of the disclosure. Referring to FIG. 5, the vehicle 1 may be configured to receive the face image of the driver from the camera 110 (210). The vehicle 1 may be configured to check a blood flow and extract a blood flow image by applying the Eulerian video magnification framework to the face image of the driver (220). The vehicle 1 may be configured to enlarge the extracted blood flow image and derive a spatiotemporal slice of the blood flow based on the enlarged blood flow image (230). The vehicle 1 may be configured to determine a pulse rate of the driver using the blood flow image and the spatiotemporal decomposition image of the blood flow (240).

Figure 6:
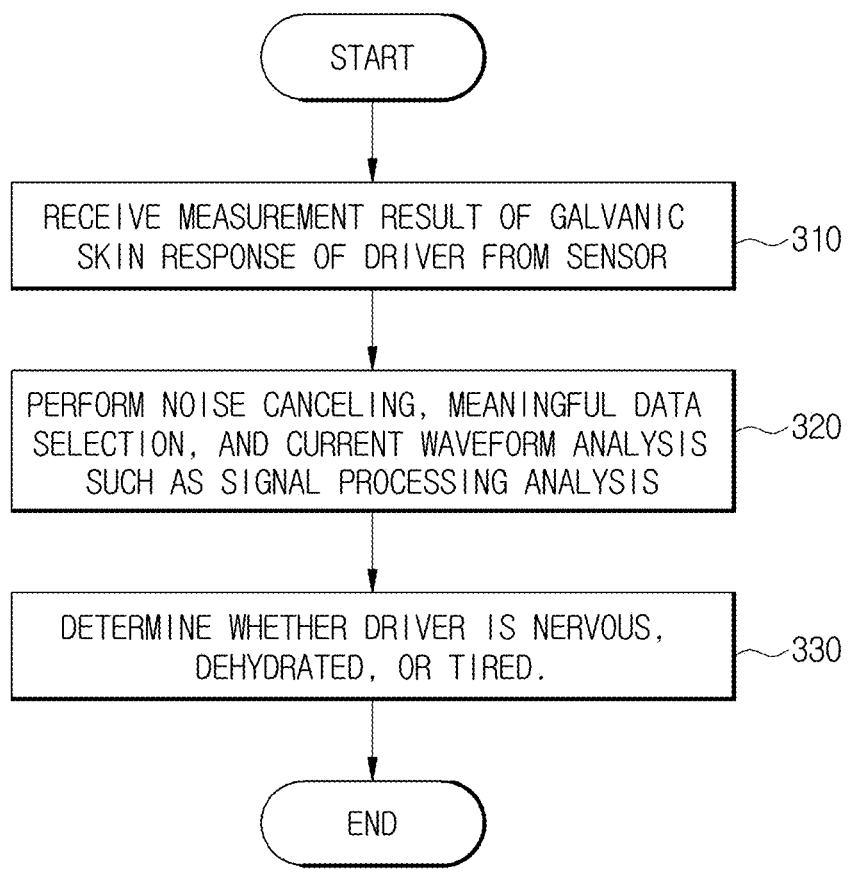
FIG. 6 illustrates a skin state measurement method according to an embodiment of the disclosure.

FIG. 6 illustrates a skin state measurement method according to an embodiment of the disclosure. Referring to FIG. 6, the vehicle 1 may be configured to receive a measurement result of the galvanic skin response from the GSR sensor 120 for measuring the galvanic skin response (310). The vehicle 1 may be configured to analyze the skin information of the driver received from the sensor 120. More specifically, the vehicle 1 may be configured to cancel a noise of galvanic skin response data, select meaningful data that satisfies a predetermined condition, perform a signal processing, and analyze a current waveform for the galvanic skin response (320).

The vehicle 1 may be configured to determine bio-signal characteristics related to the physical condition of the driver through the current waveform analysis of the galvanic skin response. For example, the vehicle 1 may be configured to determine whether the driver is temporarily nervous, whether the driver is dehydrated, how much the fatigue of the driver has accumulated, or the like based on the bio-signal characteristic (330).

Figure 7:
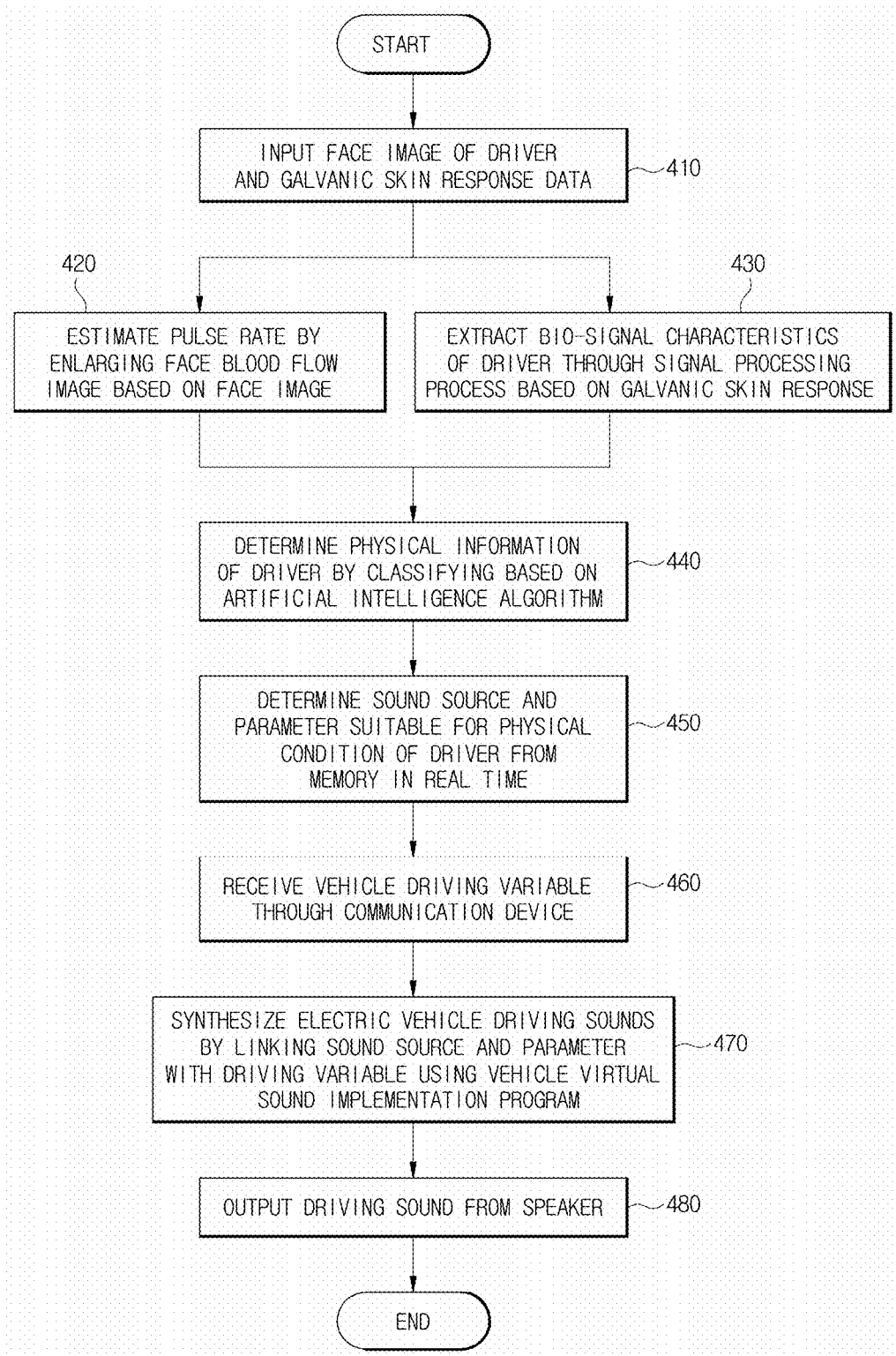
FIG. 7 illustrates a method of generating a driving sound based on driver state information according to an embodiment of the disclosure.

FIG. 7 illustrates a method of generating a driving sound based on driver state information according to an embodiment of the disclosure. The vehicle 1 may be configured to receive the face image of the driver and the galvanic skin response of the driver (410). The vehicle 1 may be configured to determine a blood flow based on the face image and enlarge the face blood flow image. The vehicle 1 may be configured to estimate the pulse rate of the driver based on the enlarged face blood flow image (420).

The vehicle 1 may be configured to extract the bio-signal characteristics of the driver through the signal processing process based on the galvanic skin response (430). The vehicle 1 may be configured to comprehensively determine a physical condition of the driver by classifying the bio-signal characteristics of the driver based on the support vector machine (SVM), which is an artificial intelligence algorithm (440).

More specifically, the vehicle 1 may be configured to comprehensively determine a physical condition of the driver based on the comprehensive analysis data for the physical condition of the driver based on the artificial intelligence algorithm and various learning models. The comprehensive analysis data for the physical condition of the driver based on the artificial intelligence algorithm and the learning models may be selectively received from the external server 2. In particular, the external server 2 may be a cloud server, but is not limited thereto.

The vehicle 1 may be configured to determine a sound source and a parameter suitable for the physical condition of the driver based on the physical condition of the driver (450). The vehicle 1 may be configured to receive the sound source and the parameter suitable for the current physical condition of the driver from the memory 150. For example, the controller 100 may be configured to determine that the physical condition of the driver is in a state in which the driver is very excited and somewhat tired, and receive the sound source and the parameter suitable for this state of the driver from the memory 150.

Additionally, the vehicle 1 may be configured to determine a sound source and a parameter suitable for the physical condition of the driver changed in real time based on the physical condition of the driver that changes in real time, and may receive the determined sound source and parameter from the memory 150 in real time. The vehicle 1 may be configured to receive the driving information through the communication device 130 (460). In this case, the driving information of the vehicle 1 may include at least one of the motor RPM, torque, accelerator pedal sensor (APS), speed, acceleration, and pedal effort.

The vehicle 1 may be configured to generate a driving sound by reflecting the driving information of the vehicle 1 in the sound source and the parameter using a virtual sound realization program. For example, the vehicle 1 may be configured to generate a driving sound by synthesizing a signal corresponding to the pedal effort with the sound source determined to be suitable for the physical condition of the driver (470). Herein, the vehicle 1 may be configured to generate a driving sound by reflecting the driving information to a sound source and a parameter suitable for the physical condition of the driver and also reflecting the tuning variable of the sound source.

The tuning variable of the sound source may include at least one of the pitch increase rate, pitch random variation, grain size, grain location, filter type, filter frequency, and shepard tone level. The vehicle 1 may be configured to output the generated driving sound from the speaker 140 (480). Conventionally, as the virtual driving sound links an electric vehicle sound source and parameter to driving conditions during driving, the electric vehicle sound source and parameter are used as files pre-tuned and saved by a vehicle manufacturer, so that the same driving sound is always output under the same driving conditions. This has a disadvantage in that only predetermined driving sounds are always output regardless of the current physical condition of the driver.

As described above, the vehicle according to an embodiment of the disclosure may determine a physical condition of the driver during driving, and may output various driving sounds in association with the driving conditions of the vehicle depending on the physical conditions of the driver.

Figure 8:
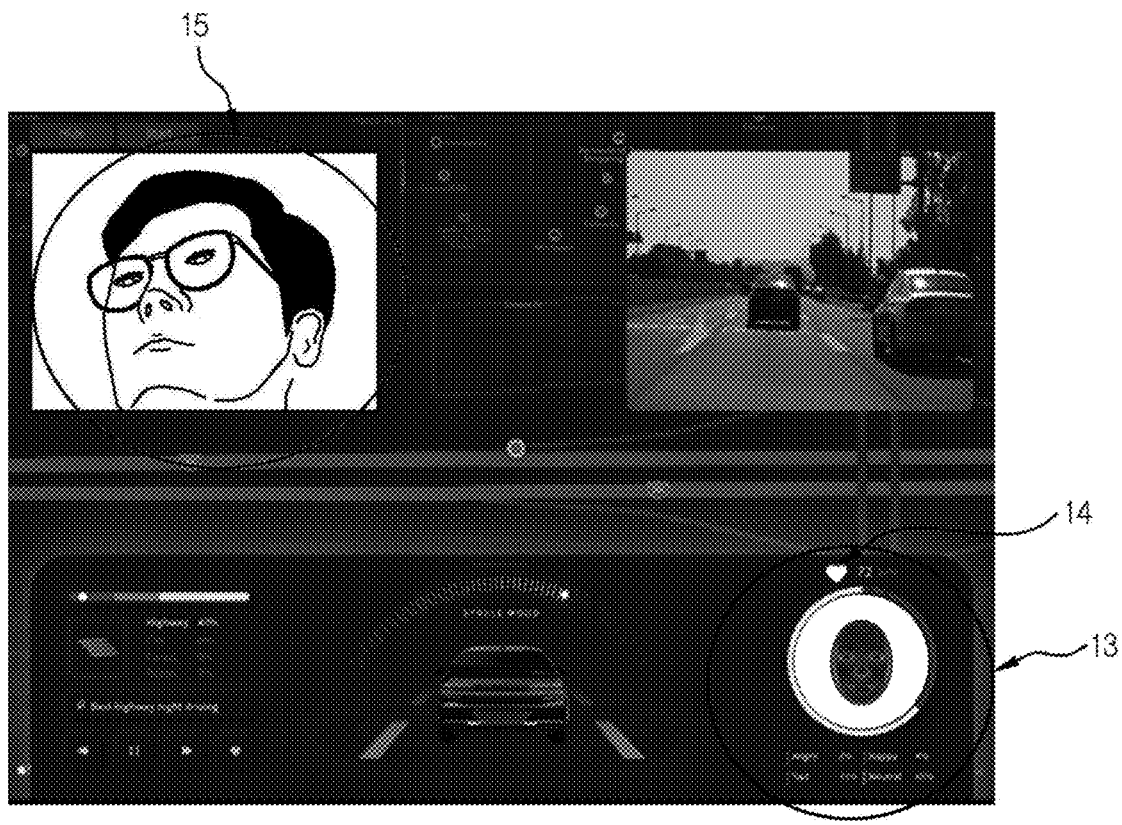
FIG. 8 is a diagram illustrating a result of the method of generating the driving sound based on the driver state information according to an embodiment of the disclosure.

FIG. 8 is a diagram illustrating a result of the method of generating the driving sound based on the driver state information according to an embodiment of the disclosure. The vehicle 1 may be configured to output the pulse rate of the driver according to the physical condition of the driver to a display device (not shown). For example, when the driver's pulse rate increases, a color of a display 14 for the pulse rate of the driver may change. Additionally, the vehicle 1 may be configured to photograph the face image of the driver 15 to estimate the pulse rate of the driver, and output the photographed image to the display device (not shown).

Herein, the disclosed embodiments may be implemented in the form of a recording medium storing instructions executable by a computer. The instructions may be stored in the form of program code, and when executed by a processor, a program module may be created to perform the operations of the disclosed embodiments. The recording medium may be implemented as a computer-readable recording medium.

The non-transitory computer-readable recording medium includes various kinds of recording media in which instructions which may be decrypted by a computer are stored. For example, there may be a ROM (Read Only Memory), a RAM (Random Access Memory), a magnetic tape, a magnetic disk, a flash memory, an optical data storage device, and the like.

As is apparent from the above, according to an embodiment of the disclosure, as a driving sound suitable for a physical condition of a driver is provided, the driver can feel greater satisfaction while driving. Further, according to an embodiment of the disclosure, as the driving sound suitable for the physical condition of the driver is provided, a driving pleasure can be provided to the driver, thereby improving the marketability of the vehicle, and in particular, in a future mobility field such as a shared vehicle, various driving sounds can be provided to suit various drivers.

The embodiments disclosed with reference to the accompanying drawings have been described above. However, it will be understood by those skilled in the art that various changes in form and details may be made therein without departing from the spirit and scope of the disclosure as defined by the appended claims. The disclosed embodiments are illustrative and should not be construed as limiting.

What is claimed is:

1. An electric vehicle, comprising:
   a camera configured to photograph a face of a driver;
   a sensor configured to obtain skin information of the driver;
   a speaker; and
   a controller configured to:
      determine a physical condition of the driver based on at least one of a face image of the driver and the skin information of the driver,
      determine a sound source and a parameter based on the physical condition of the driver,
      generate a driving sound by synthesizing a signal corresponding to driving information of the electric vehicle with the sound source and the parameter, and
      control the speaker to output the driving sound,
      wherein the driving sound includes operation sound and vibration sound of an engine; and
      wherein the driving information includes at least one of a rotation per minute (RPM) of a motor of the electric vehicle, a speed of the electric vehicle, an acceleration of the electric vehicle, and a pedal effort of the electric vehicle.

2. The electric vehicle according to claim 1, further comprising:
   a memory provided to store the sound source for each of the physical conditions and matching data of the parameter for each of the physical conditions.

3. The electric vehicle according to claim 1, wherein the controller is configured to receive the sound source and the parameter from the memory in real time based on the physical condition.

4. The electric vehicle according to claim 1, wherein the controller is configured to apply an Eulerian video magnification framework to the face image, extract a blood flow image from the face image, and estimate a pulse rate of the driver based on the blood flow image.

5. The electric vehicle according to claim 1, wherein the controller is configured to derive a spatiotemporal slice of a blood flow based on the face image.

6. The electric vehicle according to claim 1, wherein the skin information includes a galvanic skin response (GSR).

7. The electric vehicle according to claim 6, wherein the controller is configured to perform at least one of noise cancellation in data for the galvanic skin response, normalization, and selection of data satisfying a predetermined criterion.

8. The electric vehicle according to claim 1, wherein the controller is configured to determine at least one of a tension state of the driver, a dehydration state of the driver, and a fatigue state of the driver.

9. The electric vehicle according to claim 1, wherein the controller is configured to determine the physical condition using a support vector machine (SVM), which is an artificial intelligence algorithm.

10. The electric vehicle according to claim 1, wherein the controller is configured to generate the driving sound by synthesizing a tuning variable of the sound source stored in the memory with the generated driving sound; and
    wherein the tuning variable of the sound source includes at least one of a pitch increase, a pitch random variation, grain size, grain location, filter type, filter frequency, and shepard tone level.

11. A control method of an electric vehicle, comprising:
    determining, by a controller, a physical condition of a driver based on at least one of a face image of the driver and skin information of the driver;
    determining, by the controller, a sound source and a parameter based on the physical condition;
    generating, by the controller, a driving sound by synthesizing a signal corresponding to driving information of the electric vehicle with the sound source and the parameter; and
    outputting, by the controller, the driving sound;
    wherein the driving sound includes operation sound and vibration sound of an engine, and
    wherein the driving information includes at least one of a rotation per minute (RPM) of a motor of the electric vehicle, a speed of the electric vehicle, an acceleration of the electric vehicle, and a pedal effort of the electric vehicle.

12. The control method according to claim 11, further comprising:
    storing, by the controller, the sound source for each of the physical conditions and matching data of the parameter for each of the physical conditions, in a memory.

13. The control method according to claim 11, further comprising:
    receiving, by the controller, the sound source and the parameter from a memory in real time based on the physical condition.

14. The control method according to claim 11, further comprising:
    applying, by the controller, an Eulerian video magnification framework to the face image;
    extracting, by the controller, a blood flow image from the face image; and
    estimating, by the controller, a pulse rate of the driver based on the blood flow image.

15. The control method according to claim 11, further comprising:
    deriving, by the controller, a spatiotemporal slice of a blood flow based on the face image.

16. The control method according to claim 11, wherein the skin information includes a galvanic skin response (GSR).

17. The control method according to claim 16, further comprising:
    performing, by the controller, at least one of noise cancellation in data for the galvanic skin response, normalization, and selection of data satisfying a predetermined criterion.

18. The control method according to claim 11, further comprising:
    determining, by the controller, at least one of a tension state of the driver, a dehydration state of the driver, and a fatigue state of the driver.

19. The control method according to claim 11, further comprising:
    determining, by the controller, the physical condition using a support vector machine (SVM), which is an artificial intelligence algorithm.

* * * * *